United States Patent [19]

Gacek et al.

[11] 4,399,140

[45] Aug. 16, 1983

[54] 5-HALO-PYRIMIDIN-2-ONES, THE SALTS THEREOF

[75] Inventors: Mikkel Gacek; Kjell Undheim, both of Oslo, Norway

[73] Assignee: Nyegaard & Co. A/S, Norway

[21] Appl. No.: 222,959

[22] Filed: Jan. 6, 1981

[30] Foreign Application Priority Data

Jan. 7, 1980 [GB] United Kingdom ............... 8000381

[51] Int. Cl.³ ............... A61K 31/505; C07D 401/06; C07D 403/06; C07D 405/06
[52] U.S. Cl. ............... 424/251; 260/243.3; 544/295; 544/296; 544/316; 544/317; 544/318
[58] Field of Search ............... 544/295, 296, 315, 316, 544/317, 318; 424/251; 260/243.3

[56] References Cited

U.S. PATENT DOCUMENTS

| | | | |
|---|---|---|---|
| 3,833,586 | 9/1974 | Schwan et al. | 544/315 |
| 4,003,900 | 1/1977 | Schwan | 544/315 |
| 4,052,399 | 10/1977 | Schwan | 544/316 |
| 4,052,400 | 10/1977 | Schwan | 544/316 |

FOREIGN PATENT DOCUMENTS 1561290  2/1980  United Kingdom ............... 544/315

OTHER PUBLICATIONS

Gacek et al; Chem. Abs., vol. 87: 53374c, (1977).
Wibe et al; Chem. Abs., vol. 89: 192b, (1978).

Primary Examiner—Mary C. Lee
Attorney, Agent, or Firm—Bacon & Thomas

[57] ABSTRACT

Compounds of the formula:

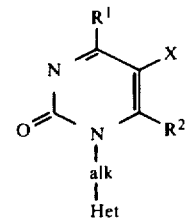

wherein
X represents a halogen atom;
$R^1$ and $R^2$, which may be same or different, each represents a hydrogen atom, or a $C_{1-4}$ alkyl group;
Het represents a C-attached 3-9 membered, saturated, unsaturated or aromatic heterocyclic ring containing one or more hetero atoms selected from O, N and S and optionally carrying a fused ring and/or optionally substituted by one or more substituents selected from halogen atoms and hydroxy, $C_{1-4}$ alkoxy, amino, acylamino, nitro, oxo, $C_{1-4}$ alkyl groups and monocyclic carbocyclic and heterocyclic aryl groups having 5 to 8 ring members; such a heterocyclic ring being saturated and having only a single heteroatom when there are 3 or 4 ring members; and
alk represents a $C_{1-4}$ saturated or unsaturated, straight or branched chain, divalent aliphatic hydrocarbyl group optionally substituted by one or more groups selected from carbocyclic aryl groups and heterocyclic groups as defined for Het above, and the salts thereof have been found to possess metaphase arresting ability which by virtue of its reversibility is of use in combating abnormal cell proliferation. Thus a knowledge of the cell division cycles of the normal and abnormal cells enables a cytotoxic drug to be administered while the abnormal cells are in a phase susceptible to attack and while the normal cells are in a non-susceptible phase.

The compounds of the invention are prepared by alkylation, ring closure of the pyrimidine ring, halogenation or ring closure of the heterocyclic ring Het.

10 Claims, No Drawings

5-HALO-PYRIMIDIN-2-ONES, THE SALTS THEREOF

The present invention relates to 5-halo-pyrimidin-2-ones having at the 1-position an alkyl group carrying a C-attached heterocycle, the salts thereof, processes for their preparation pharmaceutical compositions containing them and a method therefor.

Abnormal cell proliferation is the basic cause of a number of diseases such as cancers, leukaemias, cutaneous cellular proliferation, e.g. contact dermatitis or psoriasis, or auto-immune diseases where proliferation of lymphocytes leads to an undesirable immune response against some of the normal tissues of the body.

A number of drugs are known which combat abnormal cell proliferation by destroying the cells in one of the phases of cell-division in which they are particularly susceptible to such attack. In general, the cell division cycle of both normal and abnormal cells includes a succession of phases, usually termed the G1, S, G2 and M phases, the last-mentioned being mitosis which in itself includes four well defined phases, prophase, metaphase, anaphase and telophase, related to the rearrangement of chromosomal material in the cell. In general, DNA synthesis takes place in the S phase, while protein synthesis takes place in the G1 and G2 phases. The S phase is usually significantly longer than the G1 and G2 mitotic phases.

However, the cells are not normally dividing synchronously and at the time of administration of a particular drug a random proportion of both normal and abnormal cells will be in a phase susceptible to attack. This means that the drug is indiscriminate in its effects and if the treatment is at a dose level significantly effective against abnormal cells, a large number of body cells will also be irreversibly damaged.

The present invention is based on the concept of using a drug to arrest the cell-division cycle reversibly in a particular phase, namely the metaphase, so that during the period when an effective amount of the drug remains in the system, a large number of both normal and abnormal cells reach that phase and stop dividing. When the drug has been eliminated from the system, cell division is resumed by affected cells and is initially synchronous. However, the normal and abnormal cells usually divide at markedly different rates and, considering the cells affected by the drug, after a few hours the abnormal cells will be synchronously in one phase while the normal cells will be in another. It is then possible to administer a drug which is effective against cells in the phase reached by the abnormal cells but not effective against cells in the phase reached by the normal cells. Thus, for example, hydroxyurea and cytosine arabinoside are effective against cells in the S-phase, while vincristine and vinblastine are effective against cells in the mitotic phase.

We have found that the compounds of the invention as defined hereinafter are useful in combating abnormal cell proliferation; in particular the compounds have good metaphase arresting ability which by virtue of its reversibility is of use for this purpose.

According to one aspect of the present invention, therefore, we provide compounds of general formula I,

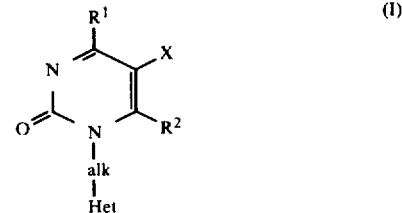

wherein

X represents a halogen atom, $R^1$ and $R^2$, which may be the same or different, each represents a hydrogen atom, or a $C_{1-4}$ alkyl group;

Het represents a C-attached 3–9 membered, saturated, unsaturated or aromatic heterocyclic ring containing one or more hetero atoms selected from O, N and S and optionally carrying a fused ring and/or optionally substituted by one or more substituents selected from halogen atoms and hydroxy, $C_{1-4}$ alkoxy, amino, acylamino, nitro, oxo, $C_{1-4}$ alkyl groups and monocyclic carbocyclic and heterocyclic aryl groups having 5–8 ring members; such a heterocyclic ring being saturated and having only a single heteroatom when there are 3 or 4 ring members; and alk represents a $C_{1-4}$ saturated or unsaturated, straight or branched chain, divalent aliphatic hydrocarbyl group optionally substituted by one or more groups selected from carbocyclic aryl groups and heterocyclic groups as defined for Het above and, where an acidic or basic group is present, the salts thereof.

The group alk is preferably an alkylene or alkenylene group having up to 3 carbon atoms.

In general, preferred substituents on the group Het are halogen atoms e.g. bromine, $C_{1-3}$ alkyl groups, e.g. methyl and alkoxycarbonyl groups.

It will be appreciated that the term "amino" as used herein includes primary, secondary and tertiary amino groups. The nitrogen atom of the amino group may therefore carry one or more $C_{1-4}$ alkyl, $C_{7-20}$ aralkyl or $C_{6-10}$ aryl groups as in the methylamino, dimethylamino or triphenylmethylamino group. Carbocyclic aryl substituents are conveniently phenyl groups. Acylamino groups, e.g. alkanoylamino, conveniently contain 1 to 4 carbon atoms, as in the acetylamino group.

As stated above the term "Het" as used herein includes 3–9 membered heterocyclic rings substituted by one or more substituents selected from for example $C_{1-4}$ alkyl, hydroxy, $C_{1-4}$ alkoxy, amino and oxo groups. It will be appreciated that when an oxo group is situated on a carbon atom of a $C_{1-4}$ alkyl group carrying a hydroxy, $C_{1-4}$ alkoxy or amino group then a carboxy, esterified carboxy or amido group will be present.

Advantageously each of $R^1$ and $R^2$, which may be the same or different, represents hydrogen or a methyl group; it is generally preferred that $R^1$ and $R^2$ are both hydrogen.

The term "a halogen atom" as used herein means a fluorine, chlorine, bromine or iodine atom.

Preferred compounds according to the present invention include compounds of formula I in which Het represents an unsaturated or aromatic heterocyclic ring optionally carrying a fused ring and/or optionally substituted.

In general, Het has 4 or more ring members, advantageously not more than 7 ring members, heterocyclic rings having 5 or 6 members being particularly preferred, 5-membered rings being especially suitable. In general, the heterocyclic group Het is preferably aromatic. Where the heterocyclic ring has another ring fused to it this way, for example, be a carbocyclic ring e.g. phenyl. In general, the heterocyclic ring preferably contains not more than two heteroatoms.

In particular for Het there may be mentioned the thienyl, isoxazolyl, pyridyl, pyrrolyl, thiazolyl, benzothienyl, furyl, diazepinyl, oxiranyl, thiiranyl, oxetanyl and thietanyl groups.

The group alk may advantageously be a methylene group. Moreover, the group alk may, for example, be substituted by an additional heterocyclic group as defined for Het which may be the same as or different from Het or alternatively by a carbocyclic aryl group, preferably having 6-10 carbon atoms e.g. phenyl.

Preferred compounds of the present invention include compounds of formula I in which Het represents a thienyl, e.g. a thien-2-yl or thien-3-yl; furyl, e.g., fur-2-yl; thiazolyl, e.g. thiazol-2-yl or thiazol-4-yl; or pyridyl, e.g. pyrid-3-yl, group.

Particularly preferred heterocyclic groups are 2-thienyl optionally substituted by methyl or bromine, 2-furyl optionally substituted by methyl, 2-thiazolyl optionally substituted by methyl and/or an ethoxycarbonyl group.

Especially preferred compounds of the present invention include the following:
1-(5-ethoxycarbonyl-4-methylthiazol-2-ylmethyl)-5-chloropyrimidin-2-one,
1-(5-bromo-2-thienylmethyl)-5-chloropyrimidin-2-one,
5-chloro-1-(5-methyl-2-furylmethyl)pyrimidin-2-one,
5-chloro-1-(3-methyl-2-thienylmethyl)pyrimidin-2-one,
5-bromo-1-(2-thienylmethyl)pyrimidin-2-one,
5-iodo-1-(2-thienylmethyl)pyrimidin-2-one,
5-chloro-1-(pyrid-3-ylmethyl)pyrimidin-2-one,
5-chloro-1-(3-thienylmethyl)pyrimidin-2-one, and
5-chloro-1-(2-thienylmethyl)pyrimidin-2-one.

Salts of compounds of formula I may include, for example, salts with alkali metal or alkaline earth metals e.g. sodium, potassium, magnesium or calcium, or ammonium (including substituted ammonium) salts. Compounds according to the invention carrying hydroxy or amino groups may also in general, possess enhanced water-solubility, the latter, of course, forming acid addition salts for example with mineral acids such as e.g. hydrochloric, perchloric or sulphuric acid or organic acids such as e.g. acetic, tartaric or citric acid.

It will be appreciated that the compounds according to the invention, depending on the groups present, may exist in a number of geometrical and/or optical forms and all such forms as well as mixtures thereof are included within the scope of the invention.

It will be further appreciated that, for pharmaceutical use, the salts referred to above will be physiologically compatible but other salts may find use, for example in the preparation of compounds of general formula I and their physiologically compatible salts.

A compound of the present invention may possess not only the ability to arrest cell proliferation, but also the ability to act as an anti-metabolite inhibiting DNA synthesis. Thus 1-2'-thienylmethyl-5-chloropyrimidin-2-one inhibits DNA synthesis in relatively high concentrations, but as the concentration decreases the metaphase arrest properties of the compound remain whilst the ability of the compound to inhibit DNA synthesis becomes less pronounced.

The compounds of the invention are structurally quite simple and may be prepared by a variety of different processes. Reactions for the preparation of the six-membered pyrimidine ring system from ureas and three carbon atom components are well known in the art.

According to another aspect of the invention, therefore, we provide a process for the preparation of a compound of the invention as defined above wherein:

(a) A compound of formula II,

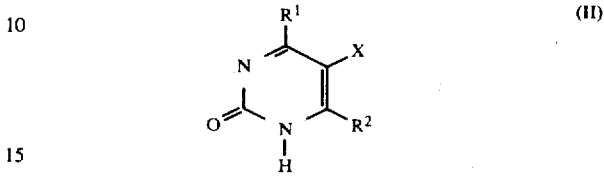

(wherein X, $R^1$ and $R^2$ are as hereinbefore defined) or a salt thereof is reacted with an agent serving to introduce the group Het—alk—, and, if desired converting a compound of formula I obtained into a salt thereof. This agent may, for example, be a compound of formula Het—alk.Y (wherein Het and alk are as hereinbefore defined and Y represents a halogen atom or a reactive ester derivative) optionally, but preferably, at an alkaline pH in the absence of water.

When the pyrimidin-2-one is used in a protonated form, the presence of a base may be an advantage as an acid binding agent e.g. an alkali metal hydroxide, such as potassium hydroxide, or an alkali metal carbonate, such as sodium carbonate, in the presence of a phase transfer catalyst such as benzyltrimethylammonium chloride. Y may represent a halogen, e.g. chlorine, bromine or iodine, atom or a reactive ester derivative for example a hydrocarbon sulphonyloxy derivative such as a mesylate, brosylate or tosylate.

The reagent serving to introduce the group Het—alk may also be an alcohol of the formula Het—alk—OH in the presence of a condensing agent such as an acetal of a $C_{1-5}$ dialkylformamide e.g. dimethyl formamide. The alkyl groups of the acetal are preferably neopentyl groups.

Alternatively, the alkylating reagent may be an acetal of the alcohol Het—alk—OH, for example, an acetal of a $C_{1-5}$ dialkylformamide carrying at least one acetal group derived from the alcohol Het—alk—OH.

The agent serving to introduce the group Het—alk— may also be an unsaturated aliphatic compound wherein the unsaturated aliphatic grouping reacts with the ring nitrogen. Such reagents include, for example olefins and acetylenes. In general, it is preferred that the unsaturated bond should be activated.

(b) A compound of formula III,

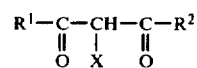

(wherein X, $R^1$ and $R^2$ are as hereinbefore defined) or a functional derivative thereof such as an enol, acetal, enol ether, enol thioether, imine or enamine derivative, is reacted with a reagent serving to replace the oxo groups or functionally equivalent groups in formula III by a urea moiety

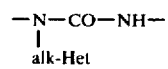

(wherein Het and alk are as hereinbefore defined) and if desired converting a compound of formula I obtained into a salt thereof.

In one variation, the compound of formula III is reacted with a urea derivative of formula IV,

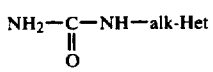

(wherein alk and Het are as hereinbefore defined).

The reaction of the compounds of formula III and IV may conveniently be effected under acid conditions, preferably in a solvent such as, for example, an alcohol, e.g. ethanol. The reaction proceeds at room temperature in the case where $R^1$ and $R^2$ are both hydrogen i.e. using a halomalondialdehyde.

The urea reagent of formula IV may, if desired, be replaced by a cyanamide of formula

(wherein Het and alk are as hereinbefore defined) which reacts to form an intermediate of formula

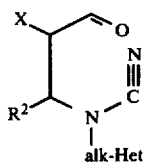

(V)

which may readily be cyclised in the presence of water to yield a compound of formula I (c) A compound of formula VI

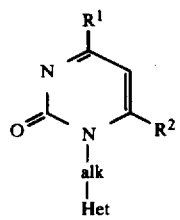

(VI)

in which $R^1$, $R^2$, alk and Het are as defined above may be converted into a corresponding compound in which X is halogen by electrophilic halogenation, e.g. using molecular chlorine or bromine, and if desired converting a compound of formula I obtained into a salt thereof.

(d) the ring closure of a compound of the formula:

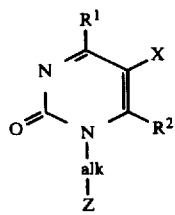

(VII)

(wherein $R^1$, $R^2$, X and alk are as hereinbefore defined and Z represents a group capable of cyclization to form the group Het as hereinbefore defined) to form a compound of formula I.

The ring closure is conveniently effected by the use of a compound of formula VII in which Z represents a group containing a free heteroatom, the closure being effected by reaction of the heteroatom to displace a leaving atom or group on an adjacent carbon atom. Thus for example the group Z may represent the group $-CH_2-CHOH-(CH_2)_nY$ (wherein Y is as hereinbefore defined, particularly a halogen atom, and n is an integer from 1 to 7). Thus where n is 1 cyclization normally in the presence of a base takes place a form an epoxide; the base in this reaction may, for example, be an inorganic base such as sodium or potassium hydroxide, or an organic base e.g. a tertiary or nitrogen base such as triethylamine.

(e) for the production of compounds of formula I in which $R^1$ is hydrogen, the removal of $-NHNH_2$ from a corresponding compound in which the 4-position of the pyrimidine carries a group $-NHNH_2$.

The removal of $-NHNH_2$ can be effected by treating the 4-hydrazinopyrimidine compound with, for example, silver oxide, conveniently in a polar solvent such as an alkanol.

The 4-hydrazinopyrimidine can be prepared by reaction of a corresponding compound in which the 4-position of the pyrimidine carries an alkylthio, e.g. methylthio group with hydrazine or a hydrate thereof, conveniently at elevated temperature in a polar solvent such as an alkanol. The 4-alkylthiopyrimidine may be prepared by introduction of the group $-Alk-Het$ into a corresponding N-unsubstituted 4-alkylthiopyrimidine, for example using the techniques described in (a) above.

Certain compounds of formula I may exist in salt form. Where acidic groupings are present in the compounds of formula I salts may be formed with alkali metal or alkaline earth metals e.g. sodium, potassium, magnesium or calcium or ammonium (including substituted ammonium) salts. Such salts may be formed in the conventional manner e.g. by reaction with sodium or potassium hydroxide. Compounds of formula I carrying amino groups may form acid addition salts e.g. with mineral acids such as hydrochloric acid or sulphuric acid or organic acids such as acetic, tartaric or citric acid. Salts of the compounds of formula I may be converted to compounds of formula I per se by conventional techniques e.g. ion exchange.

According to a yet further feature of the present invention there are provided pharmaceutical compositions comprising as active ingredient, at least one compound of formula I as hereinbefore defined or, where an acidic or basic group is present, a physiologically compatible salt thereof in association with a pharmaceutical carrier or excipient.

For pharmaceutical administration the compounds of general formula I and their physiologically compatible salts may be incorporated into the conventional preparations in either solid or liquid form.

The compositions may, for example, be presented in a form suitable for rectal, parenteral or topical administration e.g. intramuscular or intravenous administration. Preferred forms include, for example suppositories, creams, ointments and lotions, and suspensions and solutions e.g. for injection or infusion.

The active ingredient may be incorporated in excipients customarily employed in pharmaceutical compositions such as, for example, cocoa butter, aqueous or non-aqueous vehicles, fatty substances of animal or vegetable origin, paraffin derivatives, glycols, various wetting, dispersing or emulsifying agents and/or preservatives.

Advantageously the compositions may be formulated as dosage units, each unit being adapted to supply a fixed dose of active ingredient. Suitable dosage units for human adults contain from 50 mg to 1.0 g of active ingredient. The dosage, which may be varied according to the compound used, the subject treated and the complaint concerned, may, for example, be from 0.25 to 7.0 g in a day in human adults.

According to a further feature of the present invention there is provided a method of combating normal cell proliferation in a host which comprises administering to said host an effective amount of a compound of formula I or, where an acidic or basic group is present, a physiologically compatible salt thereof.

Where the compound of the invention is to be used as a metaphase arrest agent, it will normally be necessary to determine the cell division cycles, e.g. by cytofluorography or related techniques, of both the normal and abnormal cells and to prepare time schedules which indicate how long after administration of the drug the majority of the abnormal cells will reach a phase which is susceptible to attack by a chosen cytotoxic drug while the majority of normal cells are in a non-susceptible phase. These periods will naturally differ widely. Suitable cytotoxic drugs include cytosine arabinoside and hydroxyurea which are cytotoxic against cells in the S-phase. Since the S-phase is generally longer than the other phases, it is easier to find appropriate time schedules when using cytotoxic drugs active in this phase.

Where a compound of the invention such as 5-chloro-1-2'-thienylmethyl pyrimidin-2-one is used directly as an antimetabolite, it may be used alone or in conjunction with other cytotoxic drugs, according to accepted practice taking into account cell cycle considerations.

The following Examples are given by way of illustration only:

EXAMPLE 1

5-Chloro-1-(2-thienylmethyl)pyrimidin-2-one

Method A

A mixture of the potassium salt of 5-chloro-pyrimidin-2-one (70 ml) and 2-bromomethylthiophene (88 mmol) in anhydrous dimethylformamide (220 ml) was stirred at room temperature for 1 day. The solvent was distilled off at 1 mmHg, the residue dissolved in chloroform and the solution passed through a column of alumina (30 g, activity III). After evaporation of the eluate, the residue was triturated with a small volume of ether and recrystallised from ethyl acetate; yield 35%, m.p. 192° C. $^1$H NMR (TFA): δ 5.66 (CH$_2$), 7.16 (H-4), 7.41 (H-3'), 7.60 (H-5'), 8.91 (2H-4.6).

Method B

A mixture of 5-chloropyrimidin-2-one hydrochloride (8.000 g), 2-chloromethylthiophene (6.353 g), anhydrous sodium carbonate (15.237 g) and benzyltrimethylammonium chloride (0.178 g), in dimethylformamide (160 ml) was stirred and heated at 90° C. After 1.5 h more 2-chloromethylthiophene (1.226 g) was added and stirring continued. After a total of 2.5 h the reaction mixture was allowed to cool and then diluted with water (1.6 l). The resulting mixture was extracted with ethyl acetate (2×800 ml, 400 ml). The combined extracts were washed with water (2×500 ml), dried (MgSO$_4$) and evaporated to ca 100 ml during which time crystallisation occurred. The crystals were collected, washed with cold ethyl acetate and dried to give a pale cream crystalline solid (6.780 g). A second crop (1.048 g) was also obtained by concentration of the liquors. The two crops were combined and recrystallised from ethanol to give off-white crystals of the title pyrimidone, (5.990 g), m.p. 194°–196° C. (capillary), λ$_{max}$ (EtOH) 227.5 nm (ε 19,400), 327.5 nm (ε 4,500), ν$_{max}$ (CHBr$_3$) 1672 cm$^{-1}$ (C═O), (Nujol) 1664, 1652, 1645 cm$^{-1}$ (C═O).

Method C

A mixture of 5-chloropyrimidin-2-one (20 ml), N,N-dimethylformamide dineopentylacetal (30 mmol) and 2-hydroxymethylthiophene (72 mmol) in DMF (80 ml) was stirred at 80° C. for 3 h. The solvent was then removed at reduced pressure, the residue triturated with pet. ether and ether and the product chromatographed on alumina (40 g, activity III) using chloroform; yield 51%.

EXAMPLE 2

5-Chloro-1-(3,5-dimethylisoxazol-4-ylmethyl)pyrimidin-2-one

A mixture of 5-chloropyrimidin-2-one hydrochloride (0.668 g), 4-chloromethyl-3,5-dimethylisoxazole (0.874 g), anhydrous sodium carbonate (1.272 g) and benzyltrimethylammonium chloride (15 mg) in dimethylformamide (20 ml) was stirred and heated at 90° C. After 2.25 h the reaction mixture was diluted with water (200 ml) and extracted with ethyl acetate (100 ml, 2×50 ml). The combined extracts were washed with water (50 ml) and brine (50 ml), dried (MgSO$_4$) and evaporated to an orange crystalline solid (0.811 g). The solid was subjected to preparative layer chromatography (p.l.c.) on silica developing with chloroform-ethyl acetate (1:1) (two runs). The major band was eluted with chloroform-ethanol (1:1) (three times) to give a cream crystalline solid (0.313 g) which was recrystallised from ethanol to give the title pyrimidone (0.189 g) m.p. 218°–219° C. (Kofler), λ$_{max}$ (EtOH) 225 nm (ε 9,300), 310 nm (ε 2,200) inflection at 245 nm (ε 4,300) ν$_{max}$ (CHBr$_3$) 1677 cm$^{-1}$ (C═O), (Nujol) 1668 cm$^{-1}$ (C═O).

EXAMPLE 3

5-Bromo-1-(2-thienylmethyl)pyrimidin-2-one

5-Bromopyrimidin-2-one (10 mmol), 2-hydroxymethylthiophene (36 mmol) and N,N-dimethylformamide dineopentyl acetal (15 mmol) in DMF (40 ml) were heated together at 80° C. for 150 min. The coloured solution was evaporated to dryness at reduced pressure (1 mmHg), the residual viscous material triturated with pet, ether (2×25 ml) and with ether (50 ml) when it solidified. This material was dissolved in chloroform and chromatographed on alumina (20 g, activity III). The title compound was eluted with chloroform; yield 48%, m.p. 188°–190° C. (EtOAc). $^1$H NMR (TFA) δ 5.68 (CH$_2$); 7.18, 7.41, 7.58 (H3', H4', H5'), 8.95 (H4, H6).

EXAMPLE 4

5-Chloro-1-(3-methylthien-2-ylmethyl)pyrimidin-2-one (a) 2-Hydroxymethyl-3-methylthiophene Sodium borohydride (166 mg) was added portionwise over 3 mins to a stirred solution of 3-methyl-2-thiophenecarbaldehyde (0.43 ml) in ethanol (5 ml). After 25 mins acetone (1 ml) was added and then after a further 5 mins the reaction mixture was concentrated to ca 5 ml. The residue was diluted with water (20 ml) and extracted with diethyl ether (20 ml, 2×10 ml). The combined extracts were dried and evaporated to a brown liquid (490 mg). The liquid was subjected to collumn chromatography on silica (70–230 mesh) (50 g) developing with chloroform. This gave a pale brown liquid, the title thiophene (351 mg), $\lambda_{max}$ 237 nm ($E_1^1$ 538).

(b)
5-Chloro-1-(3-methylthien-2-ylmethyl)pyrimidin-2-one

N,N-Dimethylformamide dineopentyl acetal (2.70 ml) was added to a stirred suspension of 5-chloropyrimidin-2-one (783 mg) and 2-hydroxymethyl-3-methylthiophene (1.077 g) in dry N,N-dimethylformamide (15 ml) under nitrogen. The resulting solution was then heated at 90° C. under nitrogen. After 0.5 h the reaction mixture was evaporated to a dark brown crystalline solid (1.812 g). The solid was subjected to column chromatography on silica (70–230 mesh) (180 g) developing with chloroform-ethanol, 29:1. The resulting light brown crystalline solid (694 mg) was crystallised twice from acetone to give buff needles of the title thiophene (417 mg), m.p. 135°–145° C., $\lambda_{max}$ 230 nm ($\epsilon$ 16,420), 335 nm ($\epsilon$ 3,830), $\lambda_{inf}$ 250 nm ($\epsilon$ 5,800).

EXAMPLE 5

5-Chloro-1-(5-methylfurfuryl)pyrimidin-2-one

N,N-Dimethylformamide dineopentyl acetal (1.8 ml) was added to a stirred suspension of 5-chloropyrimidin-2-one (522 mg) and 2-hydroxymethyl-5-methylfuran (628 mg) in dry N,N-dimethylformamide (10 ml) under nitrogen. The resulting solution was then stirred and heated at 90° C. under nitrogen. After 1.5 h the reaction mixture was evaporated to a brown crystalline solid (1.030 g). The solid was subjected to column chromatography on silica (70–230 mesh) (100 g) developing with chloroform-ethanol, 29:1. The resulting pale yellow solid (327 mg) was crystallised twice from acetone to give white needles of the title furan (206 mg), m.p. 166°–167° C., $\lambda_{max}$ 226 nm ($\epsilon$ 15,660), 332 nm ($\epsilon$ 2,520), $\lambda_{inf}$ 247 nm ($\epsilon$ 3,100).

EXAMPLE 6

5-chloro-1-(1-methylpyrrol-2-ylmethyl)pyrimidin-2-one

N,N-Dimethylformamide dineopentyl acetal (3.04 ml) was added to a stirred suspension of 5-chloropyrimidin-2-one (881 mg) and N-methyl-2-hydroxymethylpyrrole (1.050 g) in dry N,N-dimethylformamide (17 ml) under nitrogen. The resulting pale yellow solution was then stirred and heated at 90° C. under nitrogen. After 1 h the reaction mixture was evaporated to a brown crystalline solid (1.891 g). The solid was subjected to column chromatography on silica (70–230 mesh) (200 g) developing with chloroform-ethanol, 29:1. The resulting pale brown crystalline solid (1.479 g) was crystallised twice from acetone to give off white needles of the title pyrrole (559 mg), m.p. 137°–141° C., $\lambda_{max}$ 226.5 nm ($\epsilon$ 15,920), 334 nm ($\epsilon$ 2,680).

EXAMPLE 7

5-Chloro-1-(3-thienylmethyl)pyrimidin-2-one

A mixture of 5-chloropyrimidin-2-one hydrochloride (502 mg), 3-bromomethylthiophene (1.069 g), anhydrous sodium carbonate (955 mg) and benzyltrimethylammonium chloride (12 mg) in dry N,N-dimethylformamide (15 ml) was stirred at room temperature. After 22 h the reaction mixture was diluted with water (120 ml) and the resulting precipitate was collected, washed with water and dried to give a pale yellow solid (233 mg). The solid was crystallised from ethanol to give white crystals of the title thiophene (184 mg), m.p. 194°–195° C., $\lambda_{max}$ 229 nm ($\epsilon$ 14,410), 233 nm ($\epsilon$ 3,080), $\lambda_{inf}$ 246 nm ($\epsilon$ 5,210).

EXAMPLE 8

5-Chloro-1-[2-(2-thienyl)ethyl]pyrimidin-2-one (a) 2-(2-Hydroxyethyl)thiophene tosylate Toluene-4-sulphonyl chloride (4.125 g) was added portionwise over 5 mins to an ice-cold solution of 2-(2-hydroxyethyl)thiophene (1.723 g) in anhydrous pyridine (20 ml) and the resulting pale yellow solution was stirred at 0° C. After 3 h the reaction mixture was poured into vigorously stirred water (160 ml) producing a precipitate. After cooling the solid was collected and washed with water to give white crystals of the title tosylate (3.555 g), m.p. 33°–34° C., $\lambda_{max}$ (EtOH) 227 nm ($E_1^1$ 612).

(b) 5-Chloro-1-[2-(2-thienyl)ethyl]pyrimidin-2-one

A stirred suspension of 5-chloropyrimidin-2-one (131 mg), 2-(2-hydroxyethyl)thiophene tosylate (424 mg), anhydrous sodium carbonate (265 mg) and benzyltrimethylammonium chloride (4 mg) in dry N,N-dimethylformamide (5 ml) was heated at 90° C. After 4½ h the reaction mixture was evaporated to dryness and the residue was suspended in ethyl acetate (50 ml) and washed with water (3×15 ml), dried (MgSO₄) and evaporated to a solid. The solid was subjected to p.l.c. on silica developing with chloroform-ethanol, 19:1. The more polar band was eluted with ethyl acetate and crystallised twice from acetone to give white crystals of the title pyrimidinone (94 mg), m.p. 182°–183° C., $\lambda_{max}$ (EtOH) 230 nm ($\epsilon$ 17,190), 335 nm ($\epsilon$ 3,470).

EXAMPLE 9

5-Chloro-1-(benzo[b]thien-3-ylmethyl)pyrimidin-2-one

A stirred suspension of 5-chloropyrimidin-2-one (522 mg), 2-chloromethyl benzothiophene (910 mg), anhydrous sodium carbonate (850 mg) and benzyltrimethylammonium chloride (15 mg) in dry N,N-dimethylformamide (15 ml) was stirred at room temperature for 1 h and then at 80° C. for 45 min. The reaction mixture was then diluted with water (25 ml) and extracted with ethyl acetate (75 ml, 2×25 ml). The combined extracts were washed with water (2×50 ml), dried (MgSO₄) and evaporated to a pale yellow solid which was crystallised twice from ethyl acetate to give white crystals of the title pyrimidinone (760 mg), m.p. 138°–140° C., $\lambda_{max}$ (EtOH) 227.5 nm ($\epsilon$ 32,540), 290.5 nm ($\epsilon$ 3,150), 298.5 nm ($\epsilon$ 3,760), 333.5 nm ($\epsilon$ 2,660).

EXAMPLE 10

5-Chloro-1-(2-triphenylmethylaminothiazol-4-ylmethyl)pyrimidin-2-one (a) 4-Chloromethyl-2-triphenylmethylaminothiazole A solution of 2-amino-4-chloromethylthiazole hydrochloride (3.701 g), trityl chloride (11.15 g), triethylamine (10.5 ml) and dimethylaminopyridine (10 mg) in chloroform (150 ml) was stirred at room temperature. After 23 h the reaction mixture was diluted with chloroform (150 ml) and then washed with 5% aqueous sodium hydrogen carbonate solution (2×50 ml) and brine (50 ml), dried (MgSO$_4$) and evaporated to an orange gum. The gum was triturated with diethyl ether to give a pale brown solid. The liquors from the trituration were diluted with ethyl acetate (250 ml) and washed with M-hydrochloric acid (3×60 ml), water (60 ml), and brine (30 ml) dried (MgSO$_4$) and evaporated to a pale brown foam. The triturated solid was treated in the same manner as the liquors to give a pale brown foam. The two foams were combined and subjected to column chromatography on silica developing and eluting with ethyl acetate-petrol, 1:9 and gave an off white solid (3.241 g). A portion (240 mg) of the solid was crystallised twice from ethyl acetate-petrol to give off white crystals of the title thiazole (206 mg), m.p. 139°–140° C., $\lambda_{max}$ (EtOH) 267.5 nm ($\epsilon$ 8,050).

(b)
5-Chloro-1-(2-triphenylmethylaminothiazol-4-ylmethyl)pyrimidin-2-one

A stirred suspension of 5-chloropyrimidin-2-one (688 mg), 4-chloromethyl-2-triphenylmethylaminothiazole (3.000 g), anhydrous sodium carbonate (1.086 g) and benzyltrimethylammonium chloride (20 mg) in dry N,N-dimethylformamide (25 ml) was heated at 90° C. After 1.5 h the reaction mixture was evaporated to dryness. The residue was suspended in ethyl acetate (250 ml) and washed with water (2×60 ml) and brine (60 ml), then dried and evaporated to a dark brown foam. The foam was subjected to column chromatography on silica developing and eluting with chloroform-ethanol, 24:1. This gave a brown foam which was triturated with diethyl ether to give a brown solid (2.03 g). A portion of the solid (360 mg) was recrystallised from ethyl acetate to give buff crystals of the title pyrimidinone (129 mg), m.p. 215°–216° C., $\lambda_{max}$ (EtOH) 268 nm ($\epsilon$ 8,630), 335 nm ($\epsilon$ 3,440).

EXAMPLE 11

1-(2-Acetylaminothiazol-4-ylmethyl)-5-chloropyrimidin-2-one

A stirred suspension of 5-chloropyrimidin-2-one (653 mg), 2-acetylamino-4-chloromethylthiazole (1.430 g) anhydrous sodium carbonate (1.060 g) and benzyltrimethylammonium chloride (20 mg) in dry N,N-dimethylformamide (25 ml) was heated at 90° C. After 1½ h the reaction mixture was evaporated to dryness and then the residue was suspended in ethyl acetate (250 ml) and washed with water (3×70 ml), dried (MgSO$_4$) and evaporated to a yellow foam. The foam was subjected to p.l.c. on silica developing with chloroform-ethanol, 19:1 (three runs). The major band was eluted with ethyl acetate to give a foam which was crystallised from acetone to give off white crystals of the title pyrimidinone (170 mg), m.p. 209°–211° C., $\lambda_{max}$ (EtOH) 227 nm ($\epsilon$ 11,960), 267 nm ($\epsilon$ 8,540), 334 nm ($\epsilon$ 3,420).

EXAMPLE 12

5-Chloro-1-[3-(thien-2-yl)prop-2-enyl]pyrimidin-2-one

N,N-Dimethylformamide dineopentyl acetal (6.2 ml) was added to a stirred suspension of 5-chloropyrimidin-2-one (1.802 g) and (E)-3-(thien-2-yl)prop-2-en-1-ol (2.710 g) in dry N,N-dimethylformamide (34 ml) under nitrogen and then stirring was continued at room temperature. After 3 h the reaction mixture was evaporated to dryness. The residue was dissolved in ethyl acetate (500 ml) and washed with water (3×100 ml), dried (MgSO$_4$) and evaporated to a brown gum. The gum was subjected to column chromatography on silica developing and eluting with chloroform-ethanol, 29:1. The resulting orange solid was triturated with diethyl ether to give a buff solid which was crystallised from ethyl acetate to give off white crystals of the title pyrimidinone (306 mg), m.p. 159°–161° C., $\lambda_{max}$ (EtOH) 230 nm ($\epsilon$ 10,710).

EXAMPLE 13

5-Chloro-1-(pyrid-3-ylmethyl)pyrimidin-2-one

N,N-Dimethylformamide dineopentyl acetal (1.8 ml) was added to a stirred suspension of 5-chloropyrimidin-2-one (522 mg) and 3-pyridylcarbinol (0.55 ml) in dry N,N-dimethylformamide (10 ml) under nitrogen and the mixture was then heated at 90° C. After 1 h the reaction mixture was evaporated to a brown solid which was subjected to column chromatography on silica developing one eluting with chloroform-ethanol, 14:1. This gave a pale yellow solid which was crystallised from acetone to give off white needles of the title pyrimidinone (387 mg), m.p. 191°–193° C., $\lambda_{max}$ (EtOH) 229.5 nm ($\epsilon$ 8,930), 334 nm ($\epsilon$ 2,530).

EXAMPLE 14

5-Chloro-1-(pyrid-4-ylmethyl)pyrimidin-2-one

N,N-Dimethylformamide dineopentyl acetal (1.8 ml) was added to a stirred suspension of 5-chloropyrimidin-2-one (522 mg) and 4-pyridylcarbinol (611 mg) in dry N,N-dimethylformamide (10 ml) under nitrogen and the the mixture was then heated at 90° C. After 4½ h the reaction mixture was evaporated to a brown solid which was subjected to column chromatography on silica developing and eluting with chloroform-ethanol, 14:1. This gave a yellow crystalline solid which was subjected to p.l.c. on silica developing with chloroform-ethanol, 9:1 (three runs). The major band was eluted with chloroform-ethanol, 1:1, to give a pale yellow foam which was crystallised from acetone to give off white crystals of the title pyrimidinone (210 mg), m.p. 205°–206° C., $\lambda_{max}$ (EtOH) 246 nm ($\epsilon$ 7.050), 332.5 nm ($\epsilon$ 950).

EXAMPLE 15

5-Chloro-1-(3-furylmethyl)pyrimidin-2-one

N,N-Dimethylformamide dineopentyl acetal (1.8 ml) was added to a stirred mixture of 5-chloropyrimidin-2-one (522 mg) and 3-furanmethanol (0.48 ml) in dry N,N-dimethylformamide (10 ml) under nitrogen and the mixture was then heated at 90° C. After 1¼ h the reaction mixture was evaporated to dryness and then the residue was dissolved in ethyl acetate (200 ml) and the solution washed with water (3×50 ml), dried (MgSO$_4$) and concentrated to ca 15 ml by which time crystallisation had occurred. The suspension was cooled and then the crystals collected and recrystallised from ethyl acetate to give white crystals of the title pyrimidinone (288 mg), m.p. 161.5°–162° C., $\lambda_{max}$ (EtOH) 333 nm ($\epsilon$ 2,340), $\lambda_{inf}$ 245 nm ($\epsilon$ 4,000).

EXAMPLE 16

5-Fluoro-1-(2-thienylmethyl)pyrimidin-2-one

N,N-Dimethylformamide dineopentyl acetal (1.76 ml) was added to a stirred suspension of 5-fluoropyrimidin-2-one (456 mg) and 2-hydroxymethyl thiophene (0.7 ml) in dry N,N-dimethylformamide (8 ml) under nitrogen and the mixture was then heated at 80° C. After 1 h the reaction mixture was evaporated to a brown solid which was crystallised twice from ethyl acetate to give white crystals of the title pyrimidinone (230 mg), m.p. 161°-163° C., $\lambda_{max}$ (EtOH) 222.5 nm ($\epsilon$ 10,890), 333.5 nm ($\epsilon$ 3,660).

EXAMPLE 17

5-Iodo-1-(2-thienylmethyl)pyrimidin-2-one

N,N-Dimethylformamide dineopentyl acetal (1.5 ml) was added to a stirred suspension of 5-iodopyrimidin-2-one (777 mg) and 2-hydroxymethyl thiophene (0.62 ml) in dry N,N-dimethylformamide (8 ml) under nitrogen and the mixture was then heated at 80° C. After 1¾ h the reaction mixture was evaporated to a brown solid which was crystallised twice from ethyl acetate to give the title pyrimidinone (540 mg), m.p. 207°-209° C., $\lambda_{max}$ (EtOH) 232.5 nm ($\epsilon$ 21,820), 341.5 nm ($\epsilon$ 2,420).

EXAMPLE 18

1-(5-Bromothien-2-ylmethyl)-5-chloropyrimidin-2-one

(a) 5-Bromo-2-hydroxymethylthiophene

Sodium borohydride (832 mg) was added in one portion to a stirred solution of 5-bromothiophene-2-carboxaldehyde (2.4 ml) in ethanol (50 ml) and the resulting mixture was stirred at room temperature. After 12 mins acetone (2 ml) was added and then after a further 5 mins the mixture was concentrated to ca 3 ml. The residue was partitioned between ethyl acetate (150 ml) and water (150 ml). The organic phase was separated and the aqueous phase further extracted with ethyl acetate (2×150 ml). The combined organic phases were washed with water (2×50 ml), dried (MgSO$_4$) and evaporated to a dark red liquid. Two distillations using a Kugelrohr apparatus (oven temperature 160°-165° C./0.5 mm Hg) gave a clear colourless liquid, the title alcohol (3.352 g), $n_D^{20.5}$ 1.5980, $\lambda_{max}$ (EtOH) 242.5 nm ($\epsilon$ 8,800).

(b) 1-(5-Bromothien-2-ylmethyl)-5-chloropyrimidin-2-one

N,N-Dimethylformamide dineopentyl acetal (2.25 ml) was added to a stirred suspension of 5-chloropyrimidin-2-one (653 mg) and 5-bromo-2-hydroxymethylthiophene (1.351 g) in dry N,N-dimethylformamide (12.5 ml) under nitrogen and then the mixture was heated at 40° C. After 2 h the temperature was increased to 80° C. After 4 h the reaction mixture was evaporated to dryness and the residue triturated with diethyl ether. The solid was collected and crystallised from acetone to give off white crystals of the title pyrimidinone (691 mg), m.p. 217°-220° C., $\lambda_{max}$ (EtOH) 243.5 nm ($\epsilon$ 13,810), 336 nm ($\epsilon$ 1,190).

EXAMPLE 19

1-(5-Ethoxycarbonyl-4-methylthiazol-2-ylmethyl)-5-chloropyrimidin-2-one and 1-(5-ethoxycarbonyl-2-methylthiazol-4-ylmethyl)-5-chloropyrimidin-2-one

(a) 2-Bromomethyl-5-ethoxycarbonyl-4-methylthiazole and 4-Bromomethyl-5-ethoxycarbonyl-2-methylthiazole (i) A mixture of 5-ethoxycarbonyl-2,4-dimethylthiazole (926 mg), N-bromosuccinimide (890 mg) and benzoyl peroxide (8 mg) in carbon tetrachloride (11 ml) was heated at reflux. After 1½ h the reaction mixture was allowed to cool and filtered. The filtrate was evaporated and the residual oil diluted with petrol (b.p. 40°-60° C.)-ethyl acetate, 4:1, (5 ml) resulting in the precipitation of a solid. After 1 h the suspension was filtered and the filtrate evaporated to an orange oil. Petrol (2 ml) was added to the oil resulting in the formation of a solid which after cooling was collected to give crystals of 2-bromomethyl-5-ethoxycarbonyl-4-methylthiazole (546 mg), m.p. 48°-58° C., $\lambda_{max}$ (EtOH) 266 nm ($\epsilon$ 8,640).

(ii) A mixture of 5-ethoxycarbonyl-2,4-dimethylthiazole (9.263 g), N-bromosuccinimide (8.900 g) and benzoyl peroxide (80 mg) in carbon tetrachloride (110 ml) was heated at reflux. After 3 h the reaction mixture was cooled and filterd. The filtrate was evaporated to an orange oil which was diluted with ethyl acetate-petrol (b.p. 40°-60° C.) (4:1) (50 ml). This resulted in a precipitate which was removed, the filtrate was evaporated and subjected to column chromatography on silica, developing and eluting with chloroform. This gave a pale brown solid (6.128 g) which was shown by proton N.M.R. spectroscopy to be a mixture of 2-bromomethyl-5-ethoxycarbonyl-4-methylthiazole and 4-bromomethyl-5-ethoxycarbonyl-2-methylthiazole (4:1 by h.p.l.c.).

(b) 1-(5-Ethoxycarbonyl-4-methylthiazol-2-ylmethyl)-5-chloropyrimidin-2-one and 1-(5-ethoxycarbonyl-2-methylthiazol-4-ylmethyl)-5-chloropyrimidin-2-one A mixture of 5-chloropyrimidin-2-one (914 mg) a mixture of 2-bromomethyl-5-ethoxycarbonyl-4-methylthiazole and 4-bromomethyl-5-ethoxycarbonyl-2-methylthiazole (1.484 g) and benzyltrimethylammonium chloride (26 mg) in dry N,N-dimethylformamide (35 ml) was stirred at room temperature. After 35 mins the reaction mixture was evaporated to dryness. The residue was partitioned between ethyl acetate (300 ml) and water (100 ml). The water was separated and the organic phase further washed with water (2×100 ml), dried (MgSO$_4$), then concentrated to ca 30 ml by which time crystallisation had occurred. The solid was collected to give off white crystals (1.350 g) which were subjected to column chromatography on 15 silica developing and eluting with ethyl acetate-petrol (b.p. 60°-80° C.), 1:1 at 9 p.s.i. This gave a white solid which was crystallised from chloroform-ethyl acetate to give 1-(5-ethoxycarbonyl-4-methylthiazol-2-ylmethyl)-5-chloro pyrimidin-2-one (756 mg), m.p. 169°-171° C., $\lambda_{max}$(EtOH) 230.5 nm ($\epsilon$ 12,360), 256 nm ($\epsilon$ 10,570), 334 nm ($\epsilon$ 2,950) and a less polar solid which was crystallised from ethyl acetate to give 1-(5-ethoxycarbonyl-2-methylthiazol-4-ylmethyl-5-chloropyrimidinin-2-one (171 mg), m.p. 169°-174° C., $\lambda_{max}$ (EtOH) 247 nm ($\epsilon$ 12,640), 257 nm ($\epsilon$ 11,920).

EXAMPLE 20

N-(2,4-Dihydro-5(7)-methyl-7(5)-phenyl-1H-1,4-diazepin-6-ylmethyl)-5-chloropyrimidin-2-one HCl

(a) 2,4-Dihydro-6-chloromethyl-5(7)-methyl-7(5)-phenyl-1H-1,4-diazepine HCl Paraformaldehyde (0.21 g) was added to a solution of 2,4-dihydro-5(7)-methyl-7(5)-phenyl-1H-1,4-diazepine HCl (1.45 g) in conc. HCl (10 ml). The mixture was stirred at room temperature for 15 min before the product was filtered off; yield 1.30 g. $^1$H NMR (acetone-d$_6$): δ 2.7 (Me), 3.9 (CH$_2$CH$_2$), 4.4 (CH$_2$Cl), 7.5 (Ph).

(b)

N-2,4-Dihydro-5(7)-methyl-7(5)-phenyl-1H-1,4-diazepin-6-ylmethyl)-5-chloropyrimidin-2-one HCl Finely powdered 5-chloropyrimidin-2-one (0.40 g) and triethylamine (0.3 g) were dissolved in dichloromethane (100 ml) and 2,3-dihydro-6-chloromethyl-5(7)-methyl-7-(5)-phenyl-1H-1,4-diazepine HCl (1.0 g) added. The resultant solution was heated under reflux. The white solid precipitate which was gradually formed, was collected after 2 h. and washed with acetone; yield 0.50 g, m.p. 180°–184° C. (part.decomp.). $^1$H NMR (DMSO-d$_6$): 2.33 (Me), 3.8 (CH$_2$-N), 7.3 (Ph), 7.67 and 8.33 (H-4, H-6).

EXAMPLE 21

5-Chloro-1-(2,3-epoxypropyl)pyrimidin-2-one (a)

1-(3-Bromo-2-hydroxypropyl)-5-chloropyrimidin-2-one

A stirred suspension of 5-chloropyrimidin-2-one (2.610 g), potassium carbonate (55 mg) and 1-bromo-2,3-epoxypropane (3.42 ml) in dry N,N-dimethylformamide (40 ml) was heated at 80° C. After 2¾ h the reaction mixture was evaporated and the residue was subjected to column chromatography on silica developing and eluting with chloroform-ethanol, 19:1. This gave an off white solid which was triturated with ethyl acetate to give white crystals of the title pyrimidinone (1.483 g), m.p. 166°–170° C., λ$_{max}$ (EtOH) 227 nm (ε 9,740).

(b) 5-Chloro-1-(2,3-epoxypropyl)pyrimidin-2-one

Aqueous M-sodium hydroxide solution (2.5 ml) was added to a stirred solution of 1-(3-bromo-2-hydroxypropyl)-5-chloropyrimidin-2-one (669 mg) in tetrahydrofuran (50 ml) and the mixture was stirred at room temperature. After 1 h the reaction mixture was evaporated to a yellow solid which was subjected to column chromatography on silica developing and eluting with chloroform-ethanol, 19:1. This gave a white crystalline solid which was recrystallised from ethyl acetate to give white crystals of the title pyrimidinone (59 mg), m.p. 132°–135° C., λ$_{max}$ (EtOH) 227 nm (E$_1^1$ 522), 332.5 nm (E$_1^1$ 160).

EXAMPLE 22

3-(5-Chloro-2-oxopyrimidin-1-ylmethyl)-γ-butyrolactone

A suspension of 5-chloropyrimidin-2-one (1.007 g) and sodium hydrogen carbonate (647 mg) in 3-methylene-γ-butyrolactone (1.208 g) and ethanol (50 ml) was stirred and heated at reflux. After 2 h, the suspension was cooled and filtered. The filtrate was evaporated and the residue and solid were combined and boiled in ethyl acetate (150 ml). The resulting suspension was filtered and the filtrate evaporated to a pale cream solid. The solid from the filtration was treated with water (50 ml) and the resulting suspension filtered to give a solid which was combined with the pale cream solid and recrystallised from methanol to give white crystals of the title pyrimidinone (424 mg), m.p. 283°–284° C., λ$_{max}$ (EtOH) 229.5 nm (ε 7,700), 332 nm (ε 2,100).

EXAMPLE 23

5-Chloro-1-(3-methylthietan-3-ylmethyl)pyrimidin-2-one

N,N-Dimethylformamide dineopentyl acetal (2.72 ml) was added to a stirred suspension of 5-chloropyrimidin-2-one (789 mg) and 3-hydroxymethyl-3-methylthietane (1.000 g) in dry N,N-dimethylformamide (15 ml) under nitrogen and the mixture was then heated at 100° C. After 42.5 h the reaction mixture was evaporated and the resulting black residue was dissolved in ethyl acetate (300 ml), washed with water (3×70 ml), dried (MgSO$_4$) and evaporated to a dark brown gum. Trituration of the gum with diethyl ether gave a pale brown solid which was crystallised from ethyl acetate to give cream crystals of the title pyrimidinone (110 mg), m.p. 200°–202° C., ν$_{max}$ (nujol) 1663, 1510 cm$^{-1}$ (C=O), 1612, 1582 cm$^{-1}$ (C=C, C=N).

EXAMPLE 24

5-Chloro-1-(3-methyloxetan-3-ylmethyl)pyrimidin-2-one

N,N-Dimethylformamide dineopentyl acetal (6.75 ml) was added to a stirred suspension of 5-chloropyrimidin-2-one (1.958 g) and 3-hydroxymethyl-3-methyloxetane (2.145 g) in dry N,N-dimethylformamide (37 ml) under nitrogen and the mixture was then heated at 95° C. After 44.5 h the reaction mixture was evaporated to dryness and the residue was dissolved in ethyl acetate (600 ml), washed with water (100 ml, 3×50 ml), dried (MgSO$_4$) and evaporated to a brown gum. The gum was triturated with diethylether to give a solid which was crystallised from ethyl acetate to give buff crystals of the title pyrimidinone (154 mg), m.p. 209°–211° C., ν$_{max}$ (nujol) 1670, 1570 cm$^{-1}$ (C=O), 1612, 1585 cm$^{-1}$ (C=C, C=N).

EXAMPLE 25

5-Chloro-1-(2,3-epithiopropyl)pyrimidin-2-one

A stirred suspension of 5-chloropyrimidin-2-one (730 mg, 5.6 mmol) 3-chloropropylene sulphide (680 mg, 6.2 mmol), anhydrous sodium carbonate (890 mg, 8.4 mmol) and benzyltrimethylammonium chloride (22 mg) in dry N,N-dimethylformamide (15 ml) was heated at 55° C. After 30 min the reaction mixture was diluted with water (20 ml) and extracted with ethyl acetate (×3). The combined extracts were washed with water (×2), dried (MgSO$_4$) and evaporated to a yellow solid. The solid was subjected to p.l.c. on silica developing with chloroform-ethanol, 20:1 (two runs). The major band was eluted with ethyl acetate to give a white solid which was crystallised twice from methanol to give white crystals of the title pyrimidinone (39 mg), m.p. 129°–130° C., λ$_{max}$ (EtOH) 229.5 nm (ε 8,150), 334.5 nm (ε 2,370).

EXAMPLE 26

5-Chloro-6-methyl-1-(2-thienylmethyl)pyrimidin-2-one (a)

5-Chloro-6-methyl-4-methylthio-1-(2-thienylmethyl)-pyrimidin-2-one

A suspension of 5-chloro-6-methyl-4-methylthiopyrimidin-2-one (1.768 g), 2-chloromethylthiophene (1.505 g) and potassium carbonate (2.499 g) in dry N,N-dimethylformamide (20 ml) was stirred and heated at ca 90° C. for 30 min. The reaction mixture was evaporated to dryness and the residue was partitioned between ethyl acetate (200 ml) and water (50 ml). The organic phase was washed with brine (50 ml), dried (MgSO$_4$) and evaporated to a brown solid. Preparative layer chromatography on silica developing with chloroform-ethanol (20:1, two runs) gave a solid which was crystallised from acetone to give cream crystals of the title pyrimidinone (362 mg) m.p. 173°–176° C.; $\lambda_{max}$ (EtOH) 231.5 nm ($\epsilon$ 17030), 276 nm ($\epsilon$ 9360), 320 nm ($\epsilon$ 10010).

(b)

5-Chloro-4-hydrazino-6-methyl-1-(2-thienylmethyl)-pyrimidin-2-one

A solution of 5-chloro-6-methyl-4-methylthio-1-(2-thienylmethyl)pyrimidin-2-one (987 mg) and hydrazine hydrate (98–100%) (2.5 ml) in ethanol (50 ml) was stirred and heated at reflux for one hour. The solution was evaporated to a gum which crystallised from ethanol to give pale purple crystals of the title pyrimidinone (649 mg) m.p. 184°–187° C.; $\lambda_{max}$ (EtOH) 232 nm ($\epsilon$ 14,720), 291.5 nm ($\epsilon$ 10,400).

(c)

5-Chloro-6-methyl-1-(2-thienylmethyl)pyrimidin-2-one

Silver oxide (238 mg) was added to a solution of 5-chloro-4-hydrazino-6-methyl-1-(2-thienylmethyl)-pyrimidin-2-one (128 mg) in propan-2-ol (20 ml). The mixture was stirred at ambient temperature for 24 hours, when evaporation of solvent gave a gum. This was subjected to p.l.c. on silica, developing in chloroform-ethanol (25:1, two runs). The major band was eluted with ethyl acetate giving a gum (23 mg) containing the title pyrimidinone p.m.r. spectrum in CDCl$_3$, signals relative to SiMe$_4$ in p.p.m.: 2.6 (3H, s) 6-CH$_3$; 5.4 (2H,s) 1-CH$_2$-.

EXAMPLE 27

5-Chloro-1-[4-(2-thienyl)butyl]pyrimidine-2-one

N,N-Dimethylformamide neopentyl acetal (1.7 ml) was added to a stirred suspension of 5-chloropyrimidin-2-one (520 mg) and 4-(2-thienyl)butan-1-ol (875 mg) in dry N,N-dimethylformamide (8 ml), under nitrogen, and the resulting solution was stirred at room temperature for 2 hours and then at 60° C. for 3 hours. Volatile material was removed under reduced pressure to give a yellow oil (1.64 g). Trituration with ether gave a cream solid which was recrystallised first from ethyl acetate and then from methanol to give the title pyrimidinone (225 mg) as colourless crystals m.p. 132°–133° C. $\lambda_{max}$ (EtOH) 230.5 nm ($\epsilon$ 18,300), 334 nm ($\epsilon$ 3,550).

PHARMACEUTICAL COMPOSITION EXAMPLES

Example A

| Injection solution | | |
|---|---|---|
| 1. | Active ingredient | 500 mg |
| 2. | Polysorbate 80 | 1.25 mg |
| 3. | Sodium chloride | 20 mg |
| 4. | Water for injection | to 2.5 ml |

The sterile active ingredient, comminuted as a very fine powder, is dispersed aseptically in an aqueous vehicle containing the wetting agent (Polysorbate 80) and sufficient sodium chloride to produce an approximately isotonic solution thus providing a suspension which may be used for deep intramuscular injection. Buffer salts may be incorporated (with a consequent reduction in the quantity of sodium chloride) to provide a suspension at the appropriate pH to ensure optimum stability of the compound before injection. The product may be presented as a dry filled vial of active ingredient together with a sterile ampoule of the remaining ingredients to permit extemporaneous preparation of the suspension immediately before injection.

EXAMPLE B

| Injection solution | | |
|---|---|---|
| 1. | Active ingredient | 100 mg |
| 2. | Aluminium monostearate | 5 mg |
| 3. | Fractionated coconut oil | to 1 ml |

Sterile active ingredient in the form of a very fine powder is dispersed aseptically in a sterile oily vehicle containing a suspending agent whose structure is built up during the heat sterilisation of the vehicle. Such a product may be presented as a pre-prepared suspension for intramuscular injection. The dose administered may be adjusted by alteration of the dose volume. The product may be presented in multidose vials, sealed with oil resistant rubber plugs to permit withdrawal of the required dose volume.

We claim:

1. A compound of the formula:

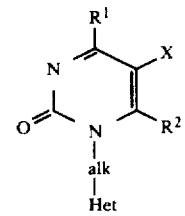

wherein

X represents a halogen atom;

R$^1$ and R$^2$, which may be the same or different, each represents a hydrogen atom or a C$_{1-4}$ alkyl group;

Het represents a C-attached 3–7 membered heterocyclic ring containing one or two heteroatoms selected from O, N and S and optionally carrying a fused ring and/or optionally carrying one or more substituents selected from the group consisting of halogen atoms and hydroxy, C$_{1-4}$ alkoxy, amino, C$_{1-4}$ alkylamino, C$_{7-20}$ aralkylamino, C$_{6-10}$ arylamino, C$_{1-4}$ alkanoylamino, nitro, oxo, C$_{1-4}$ alkyl groups and C$_{1-4}$ alkyl substituted with carboxy, C$_{1-4}$ alkyl esterified carboxy or amido groups; and monocyclic carbocyclic groups; said heterocyclic ring being saturated and having only a single heteroatom when there are 3 or 4 ring members and being unsaturated or aromatic when there are 5–7 ring members;

alk represents a C$_{1-4}$ alkylene or alkenylene group optionally substituted by a group selected from the group consisting of phenyl and 5 or 6 membered heterocyclic groups containing one or two heteroatoms selected from O, N or S; and where an acidic or basic group is present, the salts thereof.

2. Compounds as claimed in claim 1 wherein Het represents a group comprising a 5–7 membered unsaturated or aromatic heterocyclic ring.

3. Compounds as claimed in claim 2 wherein Het represents a group comprising a 5 or 6 membered heterocyclic ring.

4. Compounds as claimed in claim 1 wherein alk represents a methylene group.

5. Compounds as claimed in claim 1 wherein $R^1$ and $R^2$ each represent a hydrogen atom.

6. A compound as claimed in claim 1 which is 1-(5-carbethoxy-4-methylthiazol-2-ylmethyl)-5-chloropyrimidin-2-one,
1-(5-bromo-2-thienylmethyl)-5-chloropyrimidin-2-one,
5-chloro-1-(5-methyl-2-furylmethyl)pyrimidin-2-one,
5-chloro-1-(3-methyl-2-thienylmethyl)pyrimidin-2-one,
5-bromo-1-(2-thienylmethyl)pyrimidin-2-one,
5-iodo-(2-thienylmethyl)pyrimidin-2-one,
5-chloro-1-(pyrid-3-ylmethyl)pyrimidin-2-one,
5-chloro-1-(3-thienylmethyl)pyrimidin-2-one or
5-chloro-1-(2-thienylmethyl)pyrimidin-2-one.

7. Compounds as claimed in claim 1, wherein Het is a thienyl, furyl, thiazolyl or pyridyl group.

8. Compounds as claimed in claim 1, wherein Het is a 2-thienyl optionally substituted by methyl or bromine, 2-furyl optionally substituted by methyl or 2-thiazolyl optionally substituted by methyl and/or an ethoxycarbonyl group.

9. Pharmaceutical compositions for combatting abnormal cell proliferation comprising as active ingredient an effective amount of a compound of formula I as defined in claim 1 or, where an acidic or basic group is present, a physiologically compatible salt thereof in association with a pharmaceutical carrier or excipient.

10. A method of combating abnormal cell proliferation in a host which comprises administering to said host an effective amount of a compound of formula I as claimed in claim 1 or, where an acidic or basic group is present, a physiologically compatible salt thereof.

* * * * *